(12) United States Patent
Akiyama et al.

(10) Patent No.: US 10,119,941 B2
(45) Date of Patent: Nov. 6, 2018

(54) ELECTROSTATIC CAPACITANCE TYPE TRANSDUCER AND DRIVE METHOD THEREFOR

(71) Applicant: CANON KABUSHIKI KAISHA, Tokyo (JP)

(72) Inventors: Takahiro Akiyama, Los Angeles, CA (US); Ayako Kato, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 88 days.

(21) Appl. No.: 14/877,082

(22) Filed: Oct. 7, 2015

(65) Prior Publication Data

US 2016/0103100 A1    Apr. 14, 2016

(30) Foreign Application Priority Data

Oct. 10, 2014    (JP) .................. 2014-208859

(51) Int. Cl.
*G01N 29/24*    (2006.01)
*B06B 1/02*    (2006.01)
*B06B 1/06*    (2006.01)
*G01N 29/34*    (2006.01)

(52) U.S. Cl.
CPC ....... *G01N 29/2406* (2013.01); *B06B 1/0207* (2013.01); *B06B 1/0292* (2013.01); *G01N 29/34* (2013.01); *B06B 2201/51* (2013.01)

(58) Field of Classification Search
CPC .......... G01H 11/08; G01H 11/06; G01H 1/00; G01H 9/008; G01H 9/00; B06B 1/0292; B06B 1/0238; B06B 1/0207; G01N 29/2406; G01N 29/34

See application file for complete search history.

(56) References Cited

U.S. PATENT DOCUMENTS 3,857,092 A * 12/1974 Meyer ...................... G01B 7/02
                                                           318/662
6,461,299 B1  10/2002 Hossack
6,639,339 B1 * 10/2003 Bernstein .............. B06B 1/0292
                                                           310/311

(Continued)

FOREIGN PATENT DOCUMENTS

JP    2000-005163 A    1/2000
JP    2008-042869 A    2/2008

(Continued)

*Primary Examiner* — Helen Kwok

(74) *Attorney, Agent, or Firm* — Canon U.S.A., Inc. IP Division

(57) ABSTRACT

A drive method for an electrostatic capacitance type transducer is provided. The electrostatic capacitance type transducer includes a plurality of elements, the element including one or more cells, the cell having a first electrode and a second electrode separated from the first electrode by a gap, the first electrode or the second electrode in the plurality of elements being applied with an alternating current voltage. The plurality of elements includes a first element and a second element. A waveform of an alternating current voltage applied to the first element is set the similar as a waveform of an alternating current voltage applied to the second element. A phase difference between the alternating current voltage applied to the first element and the alternating current voltage applied to the second element is set equal to approximately 90 degrees.

19 Claims, 5 Drawing Sheets

(56) References Cited

U.S. PATENT DOCUMENTS

| | | | |
|---|---|---|---|
| 7,395,698 B2* | 7/2008 | Degertekin | B82Y 35/00 33/561 |
| 7,764,003 B2* | 7/2010 | Huang | B06B 1/0238 310/309 |
| 2007/0059858 A1* | 3/2007 | Caronti | B06B 1/0292 438/50 |
| 2008/0049954 A1* | 2/2008 | Hansen | B06B 1/0292 381/174 |
| 2010/0225333 A1* | 9/2010 | Uchida | G01D 5/2415 324/658 |
| 2012/0086307 A1* | 4/2012 | Kandori | H02N 1/006 310/300 |
| 2012/0087205 A1* | 4/2012 | Takagi | B06B 1/0292 367/13 |
| 2012/0146454 A1* | 6/2012 | Fujii | B06B 1/0292 310/300 |
| 2012/0163124 A1* | 6/2012 | Akiyama | B06B 1/0292 367/87 |
| 2012/0256518 A1* | 10/2012 | Torashima | B06B 1/0292 310/300 |
| 2012/0256519 A1* | 10/2012 | Tomiyoshi | B06B 1/0292 310/300 |
| 2012/0266682 A1* | 10/2012 | Torashima | B06B 1/0292 73/715 |
| 2014/0007693 A1* | 1/2014 | Torashima | G01H 11/06 73/658 |

FOREIGN PATENT DOCUMENTS

| | | |
|---|---|---|
| JP | 2012-143322 A | 8/2012 |
| JP | 2012-147418 A | 8/2012 |
| WO | 2005/120360 A1 | 12/2005 |
| WO | 2010/053032 A1 | 5/2010 |

* cited by examiner

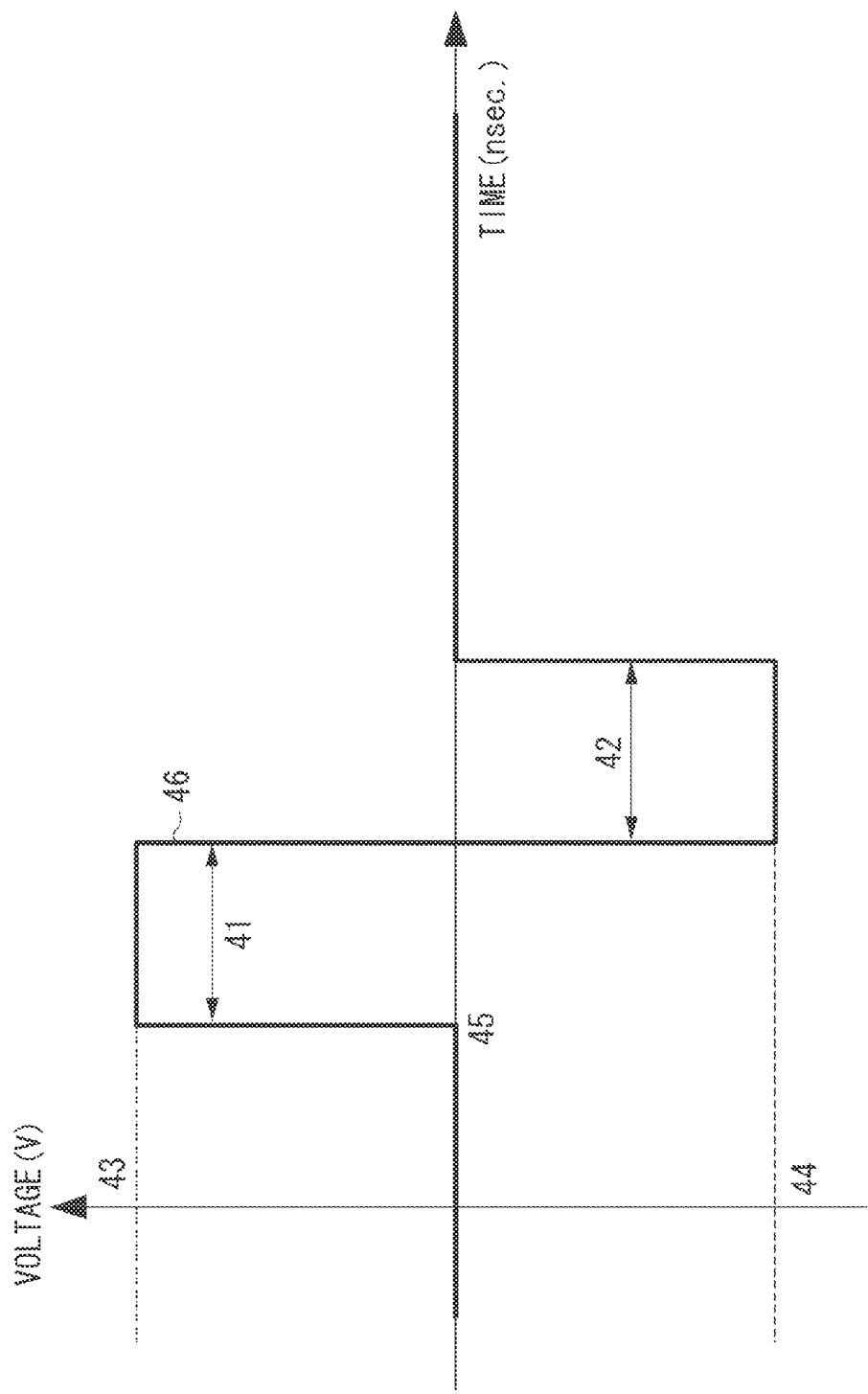

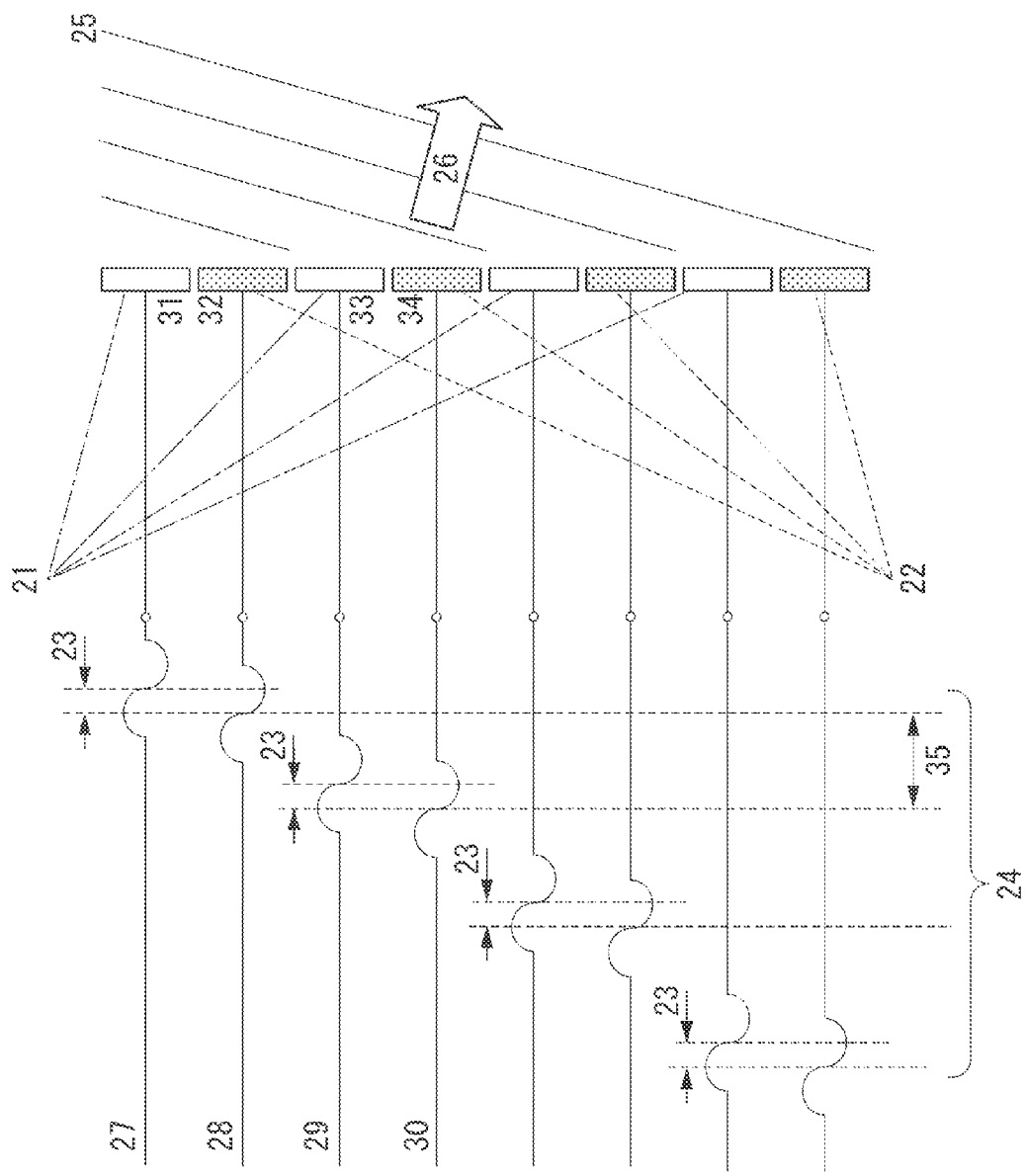

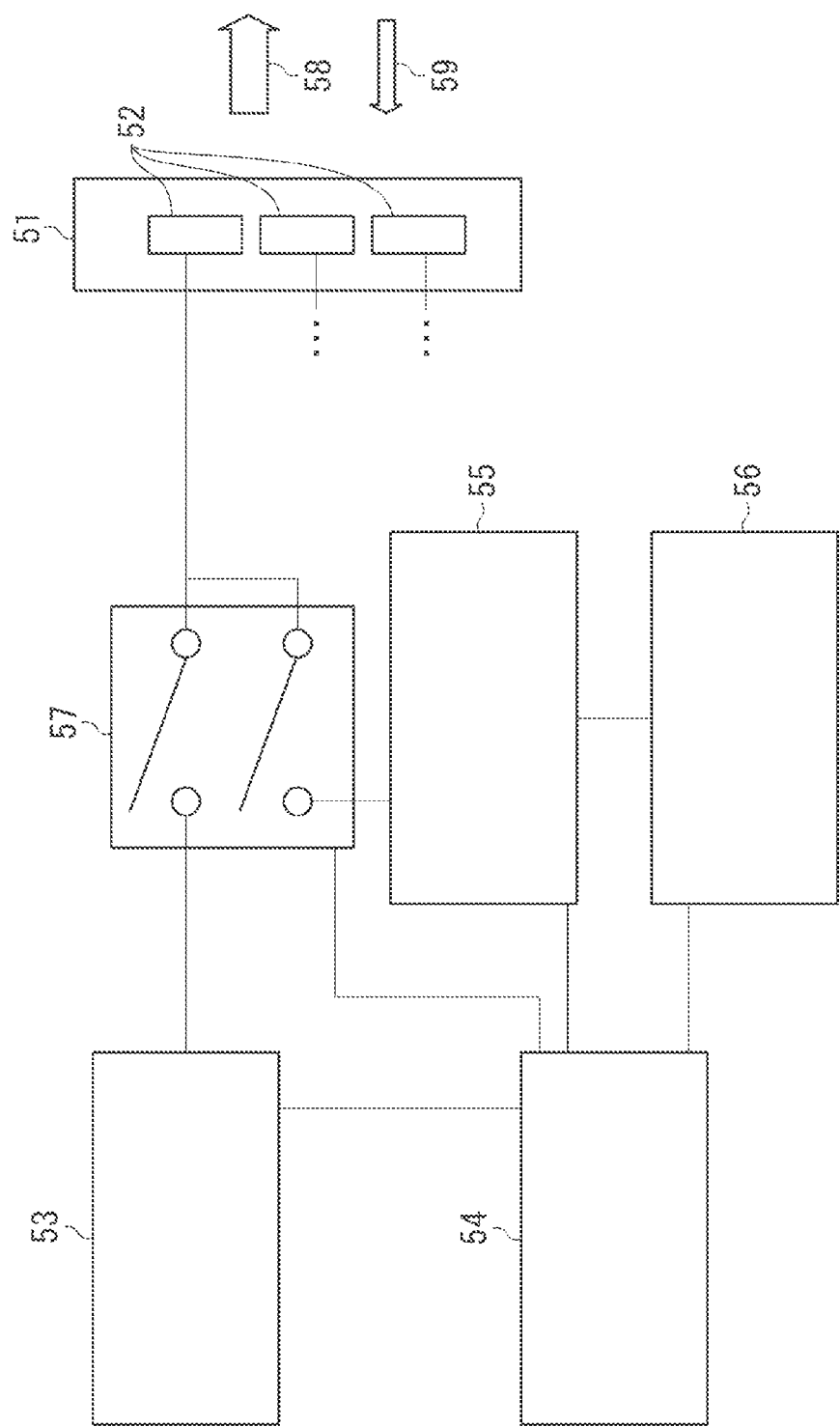

ELECTROSTATIC CAPACITANCE TYPE TRANSDUCER AND DRIVE METHOD THEREFOR

BACKGROUND

Field of the Disclosure

The present disclosure relates to an electrostatic capacitance type transducer, a drive method therefor, and a device using an electrostatic capacitance type transducer.

Description of the Related Art

Micro mechanical members manufactured using the micromachining technology have been able to be processed with micrometer precision, and various minute function elements have been implemented using the micro mechanical members. Electrostatic capacitance type transducers using such a technology are being studied as alternatives to ultrasonic transducers using piezoelectric elements. According to such electrostatic capacitance type transducers, acoustic waves, such as ultrasonic waves can be transmitted and received using vibration of a vibrating film. Especially in liquid, excellent broadband characteristics can be easily obtained using such electrostatic capacitance type transducers. The acoustic waves include sound waves, ultrasonic waves, and opto-acoustic waves. In the below description, the acoustic waves are represented by ultrasonic waves in some cases.

In the electrostatic capacitance type transducers, a conversion efficiency of an input voltage to an output sound pressure is proportional to the negative square of a distance between upper and lower electrodes. On the other hand, in a case where a large transmission sound pressure is output, it is necessary to set amplitude of a vibrating film large. In such a case, because the distance between the upper and lower electrodes varies with time, ultrasonic waves of harmonic waves having an input waveform are generated.

As a visualization technology using ultrasonic waves, there is a harmonic imaging method. The harmonic imaging method is a technique in which harmonic waves, but not a center frequency coming from a transducer, are received to generate an image. The harmonic waves are generated by nonlinearity of a density change and a sound pressure change in water and a living body tissue. When visualization according to the harmonic imaging method is performed using the electrostatic capacitance type transducer, it is predicted that harmonic waves from a tip of the transducer are mixed, because harmonic waves are generated by variation of the distance between the upper and lower electrodes with time. When harmonic waves are received, therefore, it becomes difficult to separate harmonic waves originated from a transmission sound source from harmonic waves originated from a medium to be measured. Therefore, it is desired to reduce harmonic waves included in a transmission sound pressure as far as possible. U.S. Pat. No. 6,461,299 discusses a method in which a waveform generator of a second harmonic wave is provided, and the second harmonic wave is added to a drive waveform for canceling a second harmonic wave generated as an ultrasonic wave.

SUMMARY

What kind of harmonic wave is generated depends upon the characteristics of a device and electrical characteristics around the device. Therefore, it becomes necessary to change an input waveform depending upon the manufacture variations of the device and a configuration of electrical components around the device. Therefore, it is necessary to previously measure characteristics of each transducer and adjust the waveform, which requires time and cost. Further, with such technique, it is impossible to deal with characteristic distribution among elements.

According to an aspect of the present invention, it is directed to a drive method for an electrostatic capacitance type transducer, the electrostatic capacitance type transducer including a plurality of elements, each of the plurality of elements including at least one cell, the cell having a first electrode and a second electrode separated from the first electrode, the plurality of elements including a first element and a second element, the first electrode or the second electrode in the first and second elements being applied with an alternating current voltage, the drive method comprising, setting a similar waveform of an alternating current voltage applied to the first and second elements, and setting a phase difference between the alternating current voltage applied to the first element and the alternating current voltage applied to the second element to be equal to approximately 90 degrees.

Further features of the present invention will become apparent from the following description of exemplary embodiments with reference to the attached drawings.

BRIEF DESCRIPTION OF THE DRAWINGS

FIG. 3 is a diagram illustrating an example of a drive waveform according to an exemplary embodiment of the present invention.

FIG. 4 is a diagram illustrating a configuration example of a second exemplary embodiment of the present invention.

FIG. 5 is a diagram illustrating a block configuration of a third exemplary embodiment of the present invention.

DESCRIPTION OF THE EMBODIMENTS

In an electrostatic capacitance type transducer and a drive method therefor according to an exemplary embodiment of the present invention, a phase difference between input waveforms to corresponding cells between elements is made approximately 90 degrees for a center frequency of the input waveforms, so that phases for a second harmonic wave of the center frequency become nearly opposite. The state of the corresponding cells between elements includes an example in which a plurality of cells in one element collectively corresponds to a plurality of cells in another element (see exemplary embodiments described below), and there is also a following example. When beam forming is performed, an input waveform to each of a plurality of cells in one element is provided with a predetermined phase difference as compared with a reference phase. An input waveform to each of a plurality of cells in other elements is also provided with the predetermined phase difference as compared with a reference phase, in the similar manner. In such a case, a phase difference of an input waveform between corresponding cells which are in different elements (cells to which input waveforms provided with the same predetermined phase difference as compared with the reference cell are input) is set to approximately 90 degrees as compared with a center frequency of the input waveform (see a second exemplary embodiment described below). According to an exemplary embodiment of the present invention, for example, there is little difference in characteristics between elements in close proximity and consequently it is not necessary to previously check characteristics of the elements, and the present invention can be applied to all transducers. Therefore, it is possible to provide a high-contrast electrostatic capacitance type transducer which suppresses harmonic waves generated at the time of transmission.

Figure 1A:
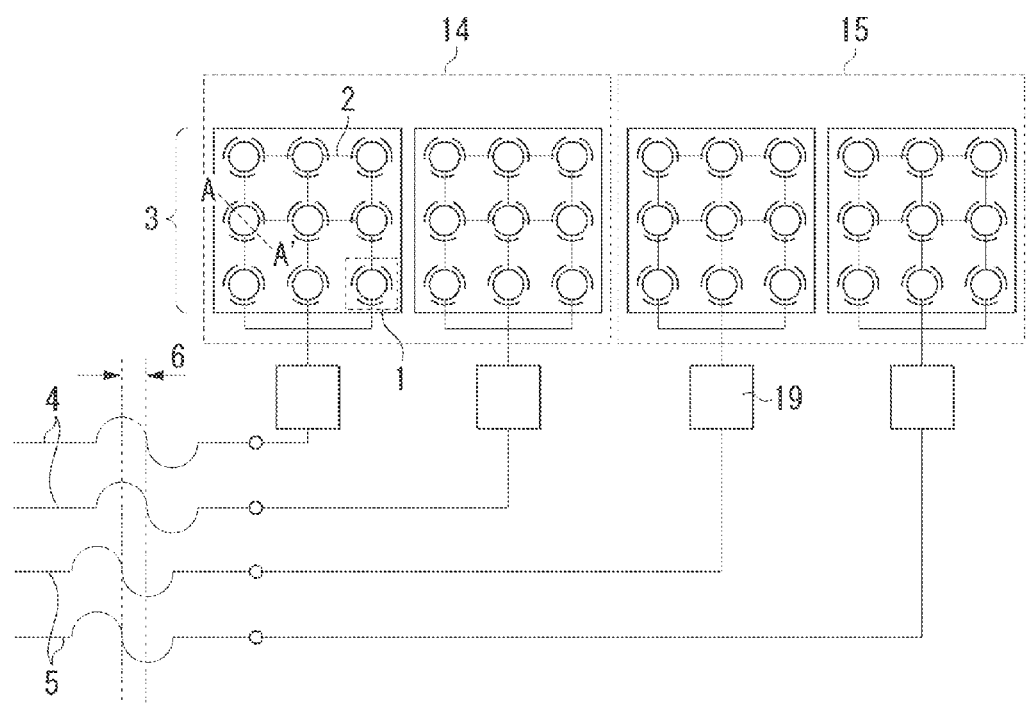
FIG. 1A is a top view illustrating an example of a drive method according to an exemplary embodiment of the present invention.
Figure 1B:
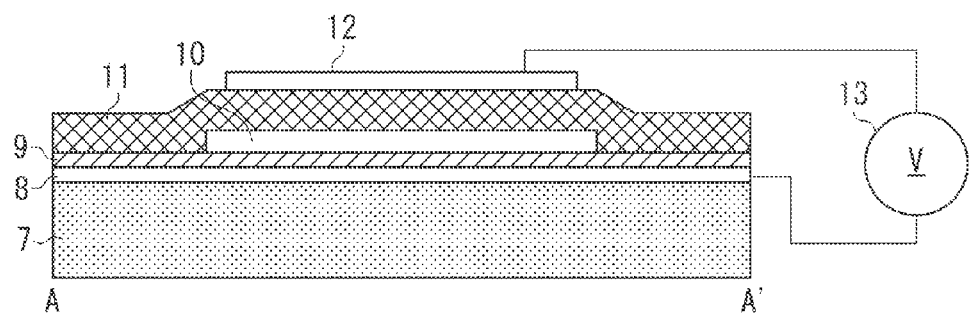
FIG. 1B is an A-A' sectional view of FIG. 1A.

An exemplary embodiment of the present invention will be described with reference to FIGS. 1A and 1B. FIG. 1A is a top view of an example of an electrostatic capacitance type transducer according to an exemplary embodiment of the present invention. FIG. 1B is an A-A' sectional view of FIG. 1A.

The electrostatic capacitance type transducer to be driven includes a plurality of elements 3 each including one or more cells 1. Cells 1 in the same element 3 are electrically connected by wiring 2. In FIG. 1A, the number of the cells 1 included in one element 3 is nine. However, the number may be arbitrary chosen. The cells 1 is arranged in a square lattice at equal intervals. Alternatively, the arrangement may be, for example, in a triangular lattice, or may be at non-equal intervals. In the electrostatic capacitance type transducer illustrated in FIG. 1A, the number of the elements 3 is four. Alternatively, the number of the elements 3 may be arbitrary as long as the number is two or more. In that case, among a plurality of elements 3, at least either of a first electrode 8 and a second electrode 12 is electrically separated. Conversely, other one of either the first electrode 8 and the second electrode 12 may be shared among the plurality of elements 3.

As illustrated in FIG. 1B, in the cell 1, a vibrating film including a second electrode 12 provided with a gap (cavity) 10 from a first electrode 8 is vibratably supported. The vibrating film includes a membrane 11 right above the gap 10 and the second electrode 12. A different film may be formed on the second electrode 12. The membrane 11 may be a conductor or semiconductor and may also serve as the second electrode 12.

The first electrode 8 (or the second electrode 12) is used as an electrode for applying a direct current (DC) bias voltage, or an electrode for applying an electric signal or taking out an electric signal. An electrode for applying the bias voltage is shared in the element 3. Although the electrode for applying the bias voltage is shared in the element 3, the electrodes for transmitting and receiving a signal must be electrically separated from element to element.

Materials included in the cell 1 in the present exemplary embodiment will be described. The first electrode 8 is formed on a substrate 7. The substrate 7 includes silicon single crystal, glass, crystallized glass, quartz, silicon carbide, sapphire, gallium arsenide, gallium phosphide, gallium nitride, and the like. It is desirable that the first electrode 8 includes metal. The first electrode 8 may be, for example, tungsten, molybdenum, titanium, aluminum, neodymium, chromium, or cobalt, or a compound or alloy of them, or a compound or an alloy of them with silicon or copper. The first electrode 8 may be a semiconductor or a compound semiconductor including high concentration impurities. When the substrate 7 is not insulative, an insulation film including, for example, silicon oxide or silicon nitride is provided between the substrate 7 and the first electrode 8.

In the present exemplary embodiment, the gap 10 is sealed in a state in which the gap 10 is sufficiently depressurized as compared with atmospheric pressure. Depressurization enhances the sensitivity of the electrostatic capacitance type transducer, and makes it possible to use the electrostatic capacitance type transducer in liquids. The first electrode 8 and the second electrode 12 are insulated by an insulator, inclusive of the gap 10. In the example of FIG. 1B, an insulation film 9 and the membrane 11 are insulators. The insulator includes, for example, silicon oxide or silicon nitride. It is desirable that the second electrode 12 includes metal. The second electrode 12 may be, for example, tungsten, molybdenum, titanium, aluminum, neodymium, chromium, or cobalt, or a compound or alloy of them, or a compound or an alloy of them with silicon or copper. In FIG. 1A, there is an electrode pad 19.

A general drive principle of the electrostatic capacitance type transducer driven by a drive method according to the present exemplary embodiment will be described. When transmitting and receiving ultrasonic waves by using a transducer, a voltage applying unit (power supply) 13 forms a voltage difference between the first electrode 8 and the second electrode 12. Then, an alternating current (AC) voltage is applied between the first electrode 8 and the second electrode 12 besides the DC voltage, the vibrating film vibrates due to a change of electrostatic force between the electrodes 8 and 12 with time. The vibration of the vibrating film is in a range of several tens kHz to several tens MHz, which is a frequency band of ultrasonic waves. It is based on a principle that an ultrasonic wave is generated by directly vibrating a substance on the vibrating film. Since an electric signal is converted to an ultrasonic wave in this way, the ultrasonic wave can be transmitted.

On the other hand, when an ultrasonic wave is received, the vibrating film including the second electrode 12 vibrates and capacitance of the element 3 changes. An AC current flows through a signal takeout electrode due to the change of the capacitance. Since the ultrasonic wave is converted to an electric signal in this way, the ultrasonic wave can be received. In a case where the electrostatic capacitance type transducer receives the ultrasonic wave, the ultrasonic wave is output as a minute AC current generated by a capacitance change. This current is converted to a voltage signal by a circuit, such as a trans-impedance amplifier.

According to an exemplary embodiment of the present invention, an image is formed from a voltage signal obtained by using the harmonic imaging method. In the harmonic imaging method, harmonic waves are generated in a process in which a transmitted ultrasonic wave propagates through a medium until the ultrasonic wave arrives at a subject. The harmonic waves are reflected by the subject and returned. The returned harmonic waves are separated from the received voltage signal by, for example, filter processing. Signal processing, for example, envelope detection is performed on the voltage signal of the separated harmonic waves. Then, conversion to a brightness value is performed on the result of the signal processing, so that brightness information on scanning lines in a direction in which the ultrasonic wave is transmitted and received is acquired. Transmission and reception of an ultrasonic wave are repeated in a plurality of directions and to a plurality of positions in the subject. As a result, brightness information on one or more scanning lines is acquired. An image inside the subject is obtained by arranging the brightness information on a plurality of scanning lines.

A characterizing drive method according to the present exemplary embodiment will be described. When an AC voltage is input to the electrostatic capacitance type transducer, the vibrating film vibrates and generates an ultrasonic wave according to transmission sensitivity characteristics of the transducer. The transmission sensitivity characteristics are proportional to an electro-mechanical conversion efficiency of the transducer. With respect to one cell, the electro-mechanical conversion efficiency is proportional to the DC bias voltage, and proportional to a capacitance change amount for a displacement of the vibrating film. When an AC component of the input voltage is sufficiently small, the inter-electrode distance can be regarded as constant with time, and consequently the capacitance change amount is constant and a sound pressure of a generated ultrasonic wave is proportional to the input voltage. The inter-electrode distance is a vacuum equivalent distance between the first electrode 8 and the second electrode 12. When it is desired to make the sound pressure large, it is necessary to make amplitude of the input AC voltage large. In this case, the inter-electrode distance largely varies with time because the vibration amplitude of the vibrating film becomes large. As a result, the generated harmonic waves are harmonic waves obtained not only by multiplying the frequency characteristics of the input AC voltage and the transmission sensitivity characteristics of the transducer, but the harmonic waves are also associated with the change of the inter-electrode distance with time. Considering the change of the inter-electrode distance with time, the electro-mechanical conversion efficiency is proportional to the negative square of the inter-electrode distance. As a result, a second harmonic wave of frequency characteristics of the input AC voltage is mainly generated.

The present invention including the present exemplary embodiment reduces the second harmonic wave. According to the present exemplary embodiment, the elements 3 are divided into a first element group 14 and a second element group 15 as illustrated in FIG. 1A. In FIG. 1A, there are two first elements 3 in the first element group 14, and two second elements 3 in the second element group 15. A plurality of elements 3 is included in each of a plurality of element groups. Alternately, it is sufficient that the first element group 14 includes one first element 3 or more and the second element group 15 includes at one second element 3 or more. In general, the number of elements included in a transducer is at least one hundred. However, each of the first element group 14 and the second element group 15 according to the present exemplary embodiment is defined as a set of elements that generate a sound pressure simultaneously at some instant. The shape and arrangement of the elements 3 in the element group do not matter. The characteristics of each of the elements 3 is nearly equivalent, a phase difference 6 between an input voltage waveform 4 to the first element group 14 and an input voltage waveform 5 to the second element group 15 is set to approximately 90 degrees.

Figure 2:
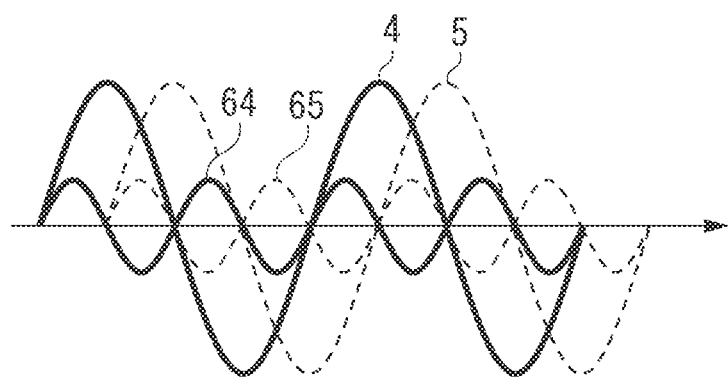
FIG. 2 is a diagram illustrating a phase difference in a case where an input voltage have a sine waveform.

As described above, the waveform of the input voltage waveform 4 and the waveform of the input voltage waveform 5 are the same and there is only the phase difference 6. As for the phase difference 6, when the input voltage waveforms 4 and 5 are sine waves, 90 degrees of a phase difference at the frequency of the sine waves is equivalent to 180 degrees in the second harmonic waves 64 and 65 as illustrated in FIG. 2. Between the first element group 14 and the second element group 15, therefore, the second harmonic waves become opposite in phase. The second harmonic waves generated on a surface of the transducer are canceled as the second harmonic waves propagate. Hereafter, the frequency of the input voltage waveforms 4 and 5 is referred to as a fundamental frequency.

In a case where the phase difference 6 at the fundamental frequency is set to 90 degrees in this way, amplitude of the second harmonic wave becomes zero. However, it is not necessary that the phase difference 6 is strictly 90 degrees, but "nearly 90 degrees" is permissible. Even if the phase difference 6 is not strictly 90 degrees, there is an effect of suppressing the second harmonic wave. For example, even if the phase difference 6 between the input voltage waveforms 4 and 5 is 80 degrees, the second harmonic wave can be reduced to 17.4%.

It is desirable that the phase difference 6 is in a range of 90±5 degrees. When the phase difference 6 is in the range of 85 to 95 degrees, the amplitude of the second harmonic wave can be reduced to 10% or less as compared with the amplitude of the second harmonic wave generated when the phase difference is 0 degree. Amplitude of the second harmonic wave generated from the electrostatic capacitance type transducer is about 10% of the ultrasonic wave amplitude at the fundamental frequency. If the second harmonic wave can be suppressed to 10% or less, an amplitude ratio of the second harmonic wave to the ultrasonic wave at the fundamental frequency becomes approximately one hundredth. The dynamic range of general ultrasonic wave imaging is about 40 decibel. When the amplitude ratio of the second harmonic wave to the ultrasonic wave at the fundamental frequency is made one hundredth or less, influence upon the video becomes sufficiently small.

The phase difference 6 sometimes deviates from 90 degrees because of a time difference of several ns caused by digitization when generating the input voltage waveforms 4 and 5. Furthermore, waveforms of the input voltage waveforms 4 and 5 sometimes distort depending upon electrical characteristics of the element 3 of the input destination. There are slight differences in electrical characteristics among the elements 3 because of configurations of the element 3 themselves and the wiring connected to the elements 3. As a result, there is a possibility that the phase difference 6 will not strictly become 90 degrees. As long as the phase difference is approximately 90 degrees, however, there is a sufficient effect of reducing the second harmonic wave as described above. Therefore, influence of electrical distortion caused by discretization errors and variations of signals is acceptable.

When each of the input voltage waveforms 4 and 5 is not a sine wave, that is, for example, even if each of the input voltage waveforms 4 and 5 is a square wave, a burst wave, a lump wave, a saw-tooth wave, or a sine wave of several wavelengths, similar effects are obtained. Therefore, the shape of the input voltage waveform is not restricted. The fundamental frequency in such a case is a center frequency at the time when the input voltage waveforms 4 and 5 are viewed in a frequency domain. The center frequency is a center point of the frequency where reduction rates as compared with a maximum value on a low frequency side and a high frequency side are equal. For example, in a frequency spectrum of the input voltage waveform, in a case where a value of a frequency where reduction of 6 decibels from a maximum value occurs is 3 MHz on the low frequency side and 9 MHz on the high frequency side, the center frequency becomes (3+9)/2=6 MHz. When 6 MHz is set to the fundamental frequency, the second harmonic wave of the fundamental frequency is 12 MHz. Then, in a case where the phase difference 6 is set to approximately 90 degrees at the fundamental frequency, an ultrasonic wave of the second harmonic wave component of the center frequency is generated on the surface of the transducer. Since the second harmonic wave components generated from the first element group 14 and the second element group 15 are opposite in phase, however, the second harmonic wave components are canceled as the second harmonic wave components propagate.

With respect to the drive method for the electrostatic capacitance type transducer, according to the present exemplary embodiment, the second harmonic wave caused by a change of the inter-electrode distance with time, which occurs at the time of transmission, is reduced. In the present exemplary embodiment, canceling of the second harmonic wave is made possible by simply making the phase difference between the input voltage waveforms approximately 90 degrees. Therefore, in the harmonic imaging method, it becomes possible to acquire clear information of second harmonic wave components generated in a medium or a living body tissue. According to the present embodiment, information based on ultrasonic waves can be clearly visualized with high contrast, because the electrostatic capacitance type transducer has essentially a wider bandwidth as compared with the piezo type transducer and generation of the second harmonic wave is suppressed as described above.

The present invention will be described in detail with reference to a more specific exemplary embodiment.

A first exemplary embodiment according to the present invention will be described with reference to FIGS. 1A and 1B. First, a section structure of the cell 1 will be described. A silicon single crystal substrate 7 obtained by forming a silicon oxide film of 100 nm is used. Tungsten having a thickness of 100 nm is used as the first electrode 8. Silicon oxide having a thickness of 100 nm is used as the insulation film 9. The gap 10 has a height of 200 nm, and is depressurized and sealed with 200 Pa. The membrane 11 on the gap 10 is a silicon nitride film, and has a thickness of 500 nm. The second electrode 12 is aluminum having a thickness of 100 nm. The vibrating film in the cell 1 has a diameter of 30 μm. The second electrode 12 has a diameter of 26 μm. The wiring 2 has a width of 5 μm.

The drive condition of the electrostatic capacitance type transducer is determined based on a pull-in voltage of the cell 1. The "pull-in" means the following phenomenon. When a DC voltage is applied between the first electrode 8 and the second electrode 12, balance between restoring force based on rigidity of the vibrating film and electrostatic force is not attained, and the vibrating film comes in contact with a bottom surface of the gap 10. This voltage is called pull-in voltage. The pull-in voltage of the cell 1 according to the present exemplary embodiment is 100 V. If the sum of the DC voltage and the input voltage waveform reaches the pull-in voltage, the vibrating film does not conduct a desired operation. Therefore, a DC voltage of 60 V is applied from the power supply 13, and the amplitude of the input voltage waveform is set to 30 V.

Per one element 3, 726 of the cells 1 are provided. The distance between centers of the cells 1 is 33 μm. The cells 1 are uniformly arranged in a square lattice form. The size of the element 3 is 4 mm in the longitudinal direction and 0.2 mm in the lateral direction. In the element 3, 121 cells are arranged in the longitudinal direction and six cells are arranged in the lateral direction. The number of elements in each of the first element group 14 including the plurality of first elements 3 and the second element group 15 including the plurality of second elements 3 is set to 16. The second harmonic wave can be reduced most by making the number of elements in the first element group 14 equal to the number of elements in the second element group 15.

$V1=30 \sin(2\pi ft)=[V]$ is input to the input voltage waveform 4, and $V2=30 \sin(2\pi ft+\pi/2)[V]$ is input to the input voltage waveform 5. Here, f is the fundamental frequency, and f is set to 8 MHz. In this case, the phase difference 6 is 90 degrees, and consequently a time difference is 31.25 ns. Under this drive condition, a wave of 16 MHz, which is the second harmonic wave, is generated from each of the elements 3. Supposing that the transmission sensitivity at the fundamental frequency of the element 3 is 10 kPa/V, an output of 300 kPa can be expected. However, it is known that the second harmonic wave that is approximately 10% of the fundamental wave is generated under this drive condition. In other words, the wave of 16 MHz is also generated by approximately 30 kPa. In the present exemplary embodiment, the phase difference between the input to the first element group 14 and the input to the second element group 15 is set to 90 degrees. With such a configuration, although the second harmonic waves are generated near the transducer, the second harmonic waves are attenuated by interference as the second harmonic waves propagate.

Similar effects are also obtained by using a waveform as illustrated in FIG. 3 as the input voltage waveform. For example, the voltage is raised to a voltage at a time 45, and the voltage 43 is kept for a time period 41. Then, the voltage is lowered to a voltage 44, and the voltage 44 is kept for a time period 42. Then, the voltage is returned to 0 V. Such a waveform is used as the input voltage waveform 4. In a case where each of the time period 41 and the time period 42 is set to 50 ns, the center frequency of the input voltage waveform is approximately 7 MHz. A waveform obtained by delaying the input voltage waveform 4 by 25 ns is used as the input voltage waveform 5. When the transducer is driven in such a manner that the input voltage waveforms have the above input voltage waveforms 4 and 5, a wideband ultrasonic wave can be generated by multiplication with transmission sensitivity characteristics of the element 3. Therefore, it is useful to imaging. Furthermore, the second harmonic wave of the center frequency is reduced by the phase difference 6.

In the drive method for the electrostatic capacitance type transducer according to the present exemplary embodiment, the second harmonic wave can be reduced regardless of individual characteristics of the transducer. As a result, unnecessary ultrasonic waves that cause noise or artifacts can be reduced. Especially in the harmonic imaging method, harmonic waves caused by the transmission sound source can be reduced. Therefore, information of the medium or the living body tissue can be clearly visualized using the drive method for the electrostatic capacitance type transducer according to the present exemplary embodiment.

A second exemplary embodiment will be described with reference to FIG. 4. An element configuration of the electrostatic capacitance type transducer is nearly the same as that in the first exemplary embodiment. An input voltage waveform 27 is input to one element in a first element group 21, for example, an element 31. At the same time, an input voltage waveform 28, which has the same waveform as the input voltage waveform 27 and has a phase difference 23 of approximately 90 degrees, is input to, for example, an element 32 in a second element group 22. An ultrasonic wave beam (acoustic wave beam) 25 is formed by providing a phase difference 24 to the entire driven elements. It is possible to control a direction 26 in which the ultrasonic wave beam 25 propagates and intensity distribution by providing the phase difference 24 suitably. In other words, one-dimensional beam forming can be conducted.

A specific drive waveform will be described. $V1=30 \sin(2\pi ft)[V]$ is input to the input voltage waveform 27, and $V2=30 \sin(2\pi ft+\pi/2)[V]$ is input to the input voltage waveform 28. Here, f is the fundamental frequency, and f is set to 8 MHz. The phase difference 23 is 90 degrees, and consequently a time difference is 31.25 ns. Under this drive condition, a wave of 16 MHz, which is the second harmonic wave, is generated from each of the elements 31 and 32. In the present exemplary embodiment, the phase difference between the input to the element 27 and the input to the element 28 is set to 90 degrees. Therefore, the second harmonic waves cancel each other and attenuate soon after the ultrasonic waves begin propagation. In the same way, V3=30 sin($2\pi ft+\Phi 1$)[V] is input to the input voltage waveform 29, and V4=30 sin($2\pi ft+\pi/2+\Phi 1$)[V] is input to the input voltage waveform 30. The second harmonic waves cancel each other because of the phase difference 23 between the input voltage waveforms 29 and 30 respectively of the elements 33 and 34. The different phase difference $\Phi 1$ corresponds to a phase difference 35 in FIG. 4. The phase difference $\Phi 1$ is a phase difference between the element 27 and the element 29, and determines a propagation direction of the ultrasonic wave. As for other elements as well, the second harmonic waves are canceled between corresponding elements in the first element group 21 and the second element group 22 by the phase difference 23, and forming of the ultrasonic wave beam 25 is controlled by the phase difference 24 between elements in the same element group.

The phase difference $\psi 1$ may be provided between elements that belong to different element groups and that are adjacent to each other in order to control the propagation direction of the ultrasonic wave. For example, V1=30 sin ($2\pi ft$)[V] is input to the input voltage waveform 27, and V2=30 sin($2\pi ft+\pi/2+\psi 1$)[V] is input to the input voltage waveform 28. If $\pi/2+\psi 1$ is in the above-described range that satisfies approximately 90 degrees in this case, there is an effect of suppressing the second harmonic wave and simultaneously, for example, an ultrasonic wave beam having a smaller side lobe can be formed.

Furthermore, the waveform 46 described in the first exemplary embodiment and illustrated in FIG. 3 may be used as the input voltage waveforms 27, 28, 29, and 30, and the phase differences 23 and 24 may be provided. In such a case, it becomes possible to cancel the second harmonic waves by determining the phase difference 23 that makes the phase difference for the center frequency of the waveform illustrated in FIG. 3 equal to approximately 90 degrees. When the frequency band of the input waveform itself is wide as in the waveform 46 in FIG. 3, a wideband ultrasonic wave can be generated in the same way as the first exemplary embodiment, which is useful to imaging.

In the configuration illustrated in FIG. 4, elements in the first element group 21 and elements in the second element group 22 are disposed alternately. Elements in close proximity are extremely close in characteristics. Therefore, nearly the same output sound pressure characteristics are obtained for the same input voltage waveform. Furthermore, generated harmonic waves become nearly the same. Therefore, the second harmonic waves are suitably canceled in a vicinity region on the ultrasonic wave output side by providing the phase difference 23 of approximately 90 degrees between to the input waveforms for corresponding adjacent elements in different element groups.

In the drive method for the electrostatic capacitance type transducer according to the present exemplary embodiment, the second harmonic wave can be reduced regardless of individual characteristics of the transducer. In addition, forming of the ultrasonic wave beam (one-dimensional beam forming) is possible. Since it becomes possible to control the frequency, measurement volume, and intensity of the ultrasonic wave by the drive method for the electrostatic capacitance type transducer according to the present exemplary embodiment, information of the desired medium and living body tissue can be visualized.

An ultrasonic wave diagnosis device (a kind of subject information acquisition device) according to a third exemplary embodiment of the present invention will be described with reference to FIG. 5. The ultrasonic wave diagnosis device transmits an acoustic wave output by the electrostatic capacitance type transducer to a subject, receives the acoustic wave from the subject, and acquires information of the subject by using the received signal. A configuration of elements 52 in an electrostatic capacitance type transducer 51 used in the present exemplary embodiment is nearly the same as that used in the first exemplary embodiment and the second exemplary embodiment. A DC voltage from the power supply 13 is applied to the electrostatic capacitance type transducer 51 as illustrated in FIG. 1B. A controller 54 provides control signals to a waveform generator (waveform generation device) 53 and a changeover switch 57, and inputs a transmission waveform of an ultrasonic wave (acoustic wave) 58. At the time of a transmission mode, a switch on a reception side turns off in the switch (switching unit) 57. The waveform generator 53 can generate an arbitrary voltage waveform.

The transmitted ultrasonic wave 58 is reflected by some substance at the propagation destination and returned to the electrostatic capacitance type transducer 51. At the time of a reception mode for receiving an ultrasonic wave 59, the controller 54 outputs a switching instruction to the switch 57. As a result, the switch on the reception side turns on and a switch on a transmission side turns off to switch the mode. In this process, the ultrasonic wave 59 is detected by the elements 52. A detected signal is processed by a signal processing system (signal processing unit) 55. A display (display unit) 56 displays an image based on data converted by the signal processing unit 55.

The controller (control unit) 53 controls input voltage waveforms and phase differences for driving the elements 52. As a result, the intensity, direction, range and frequency, and the like of the ultrasonic wave 58 applied to a measurement target (subject) can be changed freely. It is possible to acquire a wideband ultrasonic wave image with harmonic waves generated from a transducer reduced, by mounting units for executing the drive method for the electrostatic capacitance type transducer according to an exemplary embodiment of the present invention on the ultrasonic wave diagnosis device of the present exemplary embodiment.

According to an exemplary embodiment of the present invention, a phase difference between input waveforms to corresponding cells in different elements is set to approximately 90 degrees to the center frequency of the input waveforms. By doing so, nearly opposite phases are obtained for the second harmonic waves of the center frequency. As a result, components inverted in phase are generated on the surface of the transducer as regards the second harmonic waves from different elements, and the components are canceled as the components propagate.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-208859, filed Oct. 10, 2014, which is hereby incorporated by reference herein in its entirety.

What is claimed is:

1. A drive method for an electrostatic capacitance type transducer including a plurality of elements, each of the plurality of elements including at least one cell, the cell having a first electrode and a second electrode separated from the first electrode, the plurality of elements including a first element and a second element, the first electrode or the second electrode in the first and second elements being applied with an alternating current voltage, the drive method comprising:
setting a similar waveform of an alternating current voltage applied to the first and second elements; and
setting a phase difference between the alternating current voltage applied to the first element and the alternating current voltage applied to the second element to be equal to approximately 90 degrees, and
transmitting an ultrasonic wave from the first element and the second element by applying the alternating current voltage that are different in phase from each other by approximately 90 degrees to the first electrode or the second electrode of the first element and to the first electrode or the second electrode of the second element.

2. The drive method for an electrostatic capacitance type transducer according to claim 1, wherein the plurality of elements includes a first group comprising a plurality of the first elements and a second group comprising a plurality of the second element,
an alternating current voltage having a similar waveform and a same phase is applied to the first elements of the first group, and
an alternating current voltage having the similar waveform as and a phase difference of about 90 degrees from the alternating current voltage applied to the first elements in the first group is applied to the second elements in the second group.

3. The drive method for an electrostatic capacitance type transducer according to claim 1, wherein alternating current voltages having a similar waveform and provided with a phase difference for forming an acoustic wave beam are applied to each element in a first group including a plurality of the first element, and
wherein an alternating current voltage having the similar waveform as the waveform of the alternating current voltage applied to the elements in the first group and having a phase difference of approximately 90 degrees as compared with the waveform of the alternating current voltage applied to the elements in the first group, and further provided with a phase difference for forming an acoustic wave beam is applied to each element in a second group including a number of the second elements same as a number of the first elements.

4. The drive method for an electrostatic capacitance type transducer according to claim 2, wherein the alternating current voltages are applied in such a manner that the elements in the first group and the elements in the second group are alternately arranged.

5. An ultrasonic wave diagnosis device comprising:
an electrostatic capacitance type transducer configured to be driven by the drive method according to claim 1;
a power supply configured to apply a direct current (DC) voltage to the electrostatic capacitance type transducer;
a waveform generation device configured to apply alternating current voltages to the electrostatic capacitance type transducer;
a switch configured to switch a mode between a reception mode in which the DC voltage is applied to the electrostatic capacitance type transducer and a transmission mode in which the alternating current voltages are applied to the electrostatic capacitance type transducer; and
a signal processing unit configured to process a signal received by the electrostatic capacitance type transducer.

6. A subject information acquisition device comprising:
an electrostatic capacitance type transducer configured to be driven by the drive method according to claim 1,
wherein the subject information acquisition device is configured to transmit an acoustic wave output by the electrostatic capacitance type transducer to a subject, receive an acoustic wave returned from the subject, and acquire information of the subject by using the received acoustic wave.

7. The drive method for an electrostatic capacitance type transducer according to claim 1, wherein the phase difference between the alternating current voltage applied to the first element and the alternating current voltage applied to the second element is in a range of 85 to 95 degrees.

8. An electrostatic capacitance type transducer including a plurality of elements, each of the elements including one or more cells, the cell having a first electrode and a second electrode separated from a first electrode by a gap, the plurality of elements including a first element and a second element, the electrostatic capacitance type transducer comprising a waveform generation device configured to apply an alternating current voltage to the first electrode or the second electrode in the first elements and the second elements,
wherein the waveform generation device is configured to set a waveform of an alternating current voltage applied to the first element to be similar as a waveform of an alternating current voltage applied to the second element, and set a phase difference between the alternating current voltage applied to the first element and the alternating current voltage applied to the second element to be equal to approximately 90 degrees, and
wherein the electrostatic capacitance type transducer is configured to transmit an ultrasonic wave from the first element and the second element by applying the alternating current voltage that are different in phase from each other by approximately 90 degrees to the first electrode or the second electrode of the first element and to the first electrode or the second electrode of the second element.

9. The electrostatic capacitance type transducer according to claim 8, wherein the waveform generation device is configured to apply an alternating current voltage having a similar waveform and a same phase to elements in a first group including at least one or more of the first element, and
wherein the waveform generation device is configured to apply an alternating current voltage having the similar waveform as the waveform of the alternating current voltage applied to the elements in the first group and having a phase difference of approximately 90 degrees as compared with the waveform of the alternating current voltage applied to the elements in the first group to elements in a second group including a number of the second elements same as a number of the first element.

10. The electrostatic capacitance type transducer according to claim 8, wherein the waveform generation device is configured to apply alternating current voltages having a similar waveform and provided with a phase difference for forming an acoustic wave beam to each element in a first group including at least one or more of the first element, and
wherein the waveform generation device is configured to apply an alternating current voltage having the similar waveform as the waveform of the alternating current voltage applied to the elements in the first group and having a phase difference of approximately 90 degrees as compared with the waveform of the alternating current voltage applied to the elements in the first group, and further provided with a phase difference for forming an acoustic wave beam to each element in a second group including a number of the second elements same as a number of the first element.

11. The electrostatic capacitance type transducer according to claim 9, wherein the waveform generation device is configured in such a manner that the alternating current voltages are applied to the elements in the first group and the elements in the second group so that the elements in the first group and the elements in the second group are alternately arranged.

12. An ultrasonic wave diagnosis device comprising:
the electrostatic capacitance type transducer according to claim 8;
a switching unit configured to switch a mode of the electrostatic capacitance type transducer between a reception mode and a transmission mode; and
a signal processing unit configured to process a signal received by the electrostatic capacitance type transducer.

13. A subject information acquisition device comprising:
the electrostatic capacitance type transducer according to claim 8,
wherein the subject information acquisition device is configured to transmit an acoustic wave output by the electrostatic capacitance type transducer to a subject, receive an acoustic wave returned from the subject, and acquire information of the subject by using the received acoustic wave.

14. The electrostatic capacitance type transducer according to claim 8, wherein the phase difference between the alternating current voltage applied to the first element and the alternating current voltage applied to the second element is in a range of 85 to 95 degrees.

15. A drive method of an electrostatic capacitance type transducer including a plurality of elements, each of the plurality of elements including at least one cell, the cell having a first electrode and a second electrode separated from the first electrode, the plurality of elements including a first element and a second element, the first electrode or the second electrode in the first and second elements being applied with an alternating current voltage for transmitting an ultrasonic wave, the drive method comprising:
making settings to apply a first alternating current voltage to the first electrode or the second electrode of the first element and apply a second alternating current voltage to the first electrode or the second electrode of the second element;
wherein a waveform of the first alternating current voltage and a waveform of the second alternating current voltage are similar to each other; and
wherein the first alternating current voltage and the second alternating current voltage are different in phase from each other by approximately 90 degrees.

16. The drive method for an electrostatic capacitance type transducer according to claim 15, wherein the first alternating current voltage and the second alternating current voltage are different in phase from each other in a range of 85 to 95 degrees.

17. The drive method for an electrostatic capacitance type transducer according to claim 15, wherein the plurality of elements includes a first group comprising a plurality of the first elements and a second group comprising a plurality of the second elements, an alternating current voltage having a similar waveform as and a phase different of approximately 90 degrees from the alternating current voltage applied to the first elements in the first group is applied to the second elements in the second group.

18. The drive method for an electrostatic capacitance type transducer according to claim 15,
wherein alternating current voltage having a similar waveform and provided with a phase difference for forming an acoustic wave beam are applied to each element in a first group including a plurality of the first elements, and
wherein an alternating current voltage having the similar waveform as the waveform of the alternating current voltage applied to the elements in the first group and having a phase difference of approximately 90 degrees as compared with the waveform of the alternating current voltage applied to the elements in the first group, and further provided with a phase difference for forming an acoustic wave beam is applied to each element in a second group including a number of the second elements same as a number of the first elements.

19. The drive method for an electrostatic capacitance type transducer according to claim 15, wherein the first alternating current voltage and the second alternating current voltage are applied alternately.

* * * * *